United States Patent [19]

Berger et al.

[11] Patent Number: 4,551,428
[45] Date of Patent: Nov. 5, 1985

[54] AGENT FOR THE DETERMINATION OF ESTEROLYTIC AND/OR PROTEOLYTIC ENZYMES

[75] Inventors: Dieter Berger, Viernheim; Günter Frey, Ellerstadt; Wolfgang-Reinhold Knappe, Bürstadt; Manfred Kuhr, Mannheim; Walter Rittersdorf, Mannheim; Wolfgang Werner, Mannheim, all of Fed. Rep. of Germany

[73] Assignee: Boehringer Mannheim GmbH, Mannheim, Fed. Rep. of Germany

[21] Appl. No.: 260,616

[22] Filed: May 5, 1981

[30] Foreign Application Priority Data

May 9, 1980 [DE] Fed. Rep. of Germany ....... 3017721

[51] Int. Cl.$^4$ .......................... C12Q 1/44; C12Q 1/38; C12Q 1/02; C12Q 1/04; C12Q 1/06
[52] U.S. Cl. .......................................... 435/19; 435/23; 435/29; 435/34; 435/39; 435/805; 436/63; 422/56
[58] Field of Search ................. 435/4, 23, 24, 29, 805, 435/810, 34, 39, 19; 422/55, 56; 436/63; 424/7

[56] References Cited

U.S. PATENT DOCUMENTS

| 3,585,001 | 6/1971 | Mast ...................................... 436/97 |
| 3,905,872 | 9/1975 | Forgione ................................ 435/21 |
| 4,278,763 | 7/1981 | Berger et al. ......................... 435/23 |
| 4,296,202 | 10/1981 | Berger et al. ......................... 435/29 |
| 4,299,917 | 11/1981 | Berger et al. ......................... 435/23 |

FOREIGN PATENT DOCUMENTS 0025190  3/1981  European Pat. Off. .............. 435/23
1128371  of 0000  United Kingdom .

OTHER PUBLICATIONS

W. J. Williams et al.: "Haematology", 2. Ausgabe, 1977, Kapitel A25, Leukocyte esterases, Seiten 1633–1636, N.Y., U.S.A.

Primary Examiner—Esther M. Kepplinger
Attorney, Agent, or Firm—Felfe & Lynch

[57] ABSTRACT

Esters and agents including the esters, useful as substrates for esterolytic and/or proteolytic enzymes, said esters being compounds of the general formula:

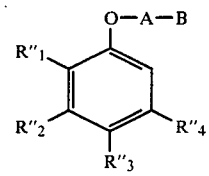

in which $R''_1$, $R''_2$, $R''_3$ and $R''_4$, which may be the same or different, are hydrogen atoms or lower alkyl, lower alkoxy, alkylamino or dialkylamino radicals or in which two adjacent substituents can also represent a fused benzene ring, A is a residue of an amino acid or of a peptide and B is a nitrogen protective group conventional in peptide chemistry or derived therefrom; and the method of preparation and use.

22 Claims, No Drawings

AGENT FOR THE DETERMINATION OF ESTEROLYTIC AND/OR PROTEOLYTIC ENZYMES

This invention relates to an agent for the detection of esterolytic and/or proteolytic enzymes and the substrates suitable therefor.

In the diagnosis of diseases of the kidneys and of the urogenital tract, the detection of leukocytes in the urine is of great importance. Hitherto, this detection was carried out microscopically by counting under a microscope the number of leukocytes present in a particular volume of urine. However, this method is very laborious, time-consuming and tiring and, in addition, requires the use of trained personnel.

Consequently, for some time, as a detection principle for leukocytes in various body fluids, use has been made of enzymatic reactions since leukocytes possess a broad spectrum of enzymatic activity.

Agents for the detection of leukocytes in body fluids in which the esterolytic and/or proteolytic activity present in the leukocytes is utilized for analytical purposes are known from Federal Republic of Germany Patent Specifications Nos. 28 26 965 and 28 36 644, sulphonphthalein esters and azo dyestuff esters, respectively, thereby being used as substrates for the leukocyte esterases and/or proteases. The colored materials liberated by the enzymatic reaction are evaluated by generally known methods. However, the agents described in these Patent Specifications are still too insensitive. They have reaction times which are too long for the lower limits of detection so that the practical use thereof still involves certain disadvantages, especially too long waiting times in the carrying out of the test.

Various methods for the detection of proteases and esterases are also known from histo- and cytochemical enzymology (cf., for example, A. G. E. Pearse, Histochemistry, Theoretical and Applied, 3rd edn., pub. Churchill-Livingstone, Edinburgh, London, New York, 1968). In principle, colorless or weakly colored esters are thereby used which, by means of enzymatic splitting, mostly break down into a colorless acid and an also colorless alcohol or phenol component. The latter is then reacted, in a reaction following the enzymatic saponification, to give colored products, for example, by coupling with diazonium salts or by an oxidative reaction.

F. Schmalzl and H. Braunsteiner described, for example, in Klin. Wschr., 46, 642/1968, a specific cytochemical leukocyte esterase detection with naphthol AS-D-chloroacetate as substrate and a diazonium salt for the formation of the colored azo compound.

However, two-component systems of this type have proved to be unsuitable as agents for the rapid and simple detection of leukocytes in body fluids, such as urine. They react much too insensitively. Thus, for example, samples containing 5000 leukocytes/$\mu$l. do not show any reaction. Furthermore, as is known, many compounds present in urine, such as urobilinogen, stercobilinogen, bilirubin and the like, react with diazonium salts. This is best illustrated by patented and commercially available tests for the detection of urobilinogen or bilirubin in urine which use diazonium salts for the detection reaction. The diazonium salts used in the literature for the detection of esterases show the above-described side reactions with other components of the urine and are, in some cases, also unsuitable for a leukocyte test because of their inherent color.

It is an object of the present invention to provide an agent for the detection of esterolytic and/or proteolytic enzymes with a combination of esters and diazonium salts as reaction components for these enzymes with which these can be detected in a simple manner in a short time in a manner which is easily carried out and which does not display any disturbing side reactions with other components of the sample to be investigated.

This object is achieved by a definite combination of appropriate esters and especially substituted diazonium salts, the diazonium salts thereby surprisingly not entering into any side reactions with other components of the urine, for example bilirubin or urobilinogen, but, on the contrary, couple specifically and quickly with the phenolic components resulting from the splitting of the esters used, with the formation of a colored compound.

The esters used must be sufficiently reactive with regard to the esterolytic and/or proteolytic enzymes in order that they are split as quickly as possible into the acid and alcohol components, by which phenols are also to be understood. The esters are also to be selected in such a manner that the liberated alcohol component couples well and completely with the diazonium salts used. The reactivity of the diazonium salts must, by appropriate selection of the substituents, be adjusted in such a manner that a sufficiently rapid coupling with the alcohol components liberated from the esters employed according to the present invention definitely takes place but that no reaction occurs with other components of the test solution.

Therefore, the present invention provides an agent for the detection of esterolytic and/or proteolytic enzymes and especially of the esterases and/or proteases present in leukocytes, consisting of an absorbent carrier, a film layer, a powder mixture, a lyophilizate, a solution or a reagent tablet containing an appropriate esterase and/or protease detection principle, a buffer and optionally other conventionally employed additives, wherein the esterase and/or protease detection principle used is a combination of a specially substituted diazonium salt and an appropriate ester, the reactivity of which is mutually coordinated by appropriate selection of the substituents in such a manner that a sufficiently rapid coupling takes place with the alcohol component liberated from the ester but no reaction with other components of the test solution occurs.

Appropriate substituted diazonium salts for use according to the present invention are, for example, compounds of the general formula:

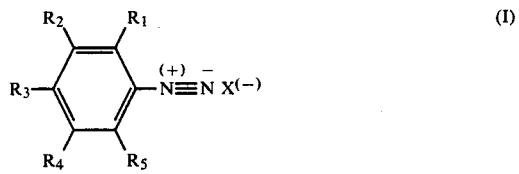

wherein $R_1$ is a lower alkyl, lower alkoxy, lower alkylthio, N-morpholino, N-thiomorpholino, N-pyrrolidino, optionally N'-alkylated N-piperazino or N-piperidino radical or is a hydrogen or halogen atom, $R_3$ is a lower alkyl, lower alkoxy, aryloxy, lower alkylthio, alkylamino, dialkylamino, hydroxyl, N-morpholino, N-thiomorpholino, N-pyrrolidino, optionally N'-alkylated N-piperazino, N-piperidino or phenylamino radical or a phenyl radical optionally substituted with a lower alkyl or lower alkoxy radical or is a hydrogen or halogen atom, $R_2$, $R_4$ and $R_5$, which may be the same or different, are lower alkyl, lower alkoxy or lower alkylthio radicals or hydrogen or halogen atoms and X is a stabilizing anion.

Appropriate esters which can be used according to the present invention are, for example, compounds of the general formula:

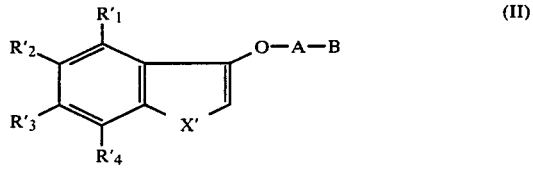
(II)

wherein $R'_1$, $R'_2$, $R'_3$ and $R'_4$, which may be the same or different, are hydrogen or halogen atoms or lower alkyl, lower alkoxy, aryl, aralkyl, aralkoxy, hydroxyl, carboxy, carboxy lower alkoxy, aralkoxycarbonyl, aralkoxycarbonyl lower alkoxy, nitro or lower acylamino radicals or wherein two adjacent substituents can also represent an optionally halogen-substituted fused benzene ring, X' is a sulphur atom or an imino group optionally substituted by a lower alkyl, aryl, aralkyl or acyl radical, A is the residue of an amino acid or of a peptide and B is a nitrogen protective group conventional in peptide chemistry or derived therefrom; or compounds of the general formula:

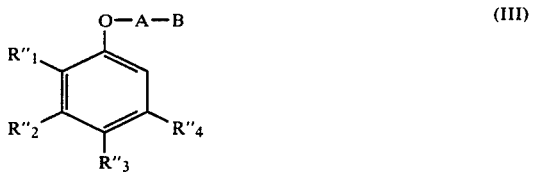
(III)

wherein $R''_1$, $R''_2$, $R''_3$ and $R''_4$, which may be the same or different, are hydrogen atoms or lower alkyl, lower alkoxy, alkylamino or dialkylamino radicals or wherein two adjacent substituents can also represent a fused benzene ring and A and B have the same meanings as above.

The esters of general formulae (II) and (III) are rapidly and completely saponified by esterases and/or proteases, for example by the esterases and proteases present in neutrophilic granulocytes. The liberated phenol components react well, quickly and selectively with the low electrophilic diazonium salts of general formula (I). Therefore, according to the principle of the present invention, stable and rapidly indicating agents for the detection of leukocytes in body fluids can be produced. Furthermore, we have found that the agents according to the present invention are also outstandingly useful for the general detection of proteolytic enzymes, for example of elastase, chymotrypsin or trypsin, in aqueous solutions or in body fluids, for example whole blood, serum and liquors, pancreas secretion and aqueous faecal extracts.

Some of the diazonium salts of general formula (I) are known compounds. Derivatives in which the symbols $R_1$ and/or $R_3$ represent an N-thiomorpholino, N-pyrrolidino, an optionally N'-alkylated N-piperazino or an N-piperidino radical are new compounds. However, they can be prepared analogously to known compounds by known methods.

The compounds of general formula (II) are described in Federal Republic of Germany Patent Specification No. 28 54 987 (corresponds to U.S. Pat. No. 4,278,763, for which it is a priority application).

The esters of general formula (III) are new compounds. They can be prepared by reacting a compound of the general formula:

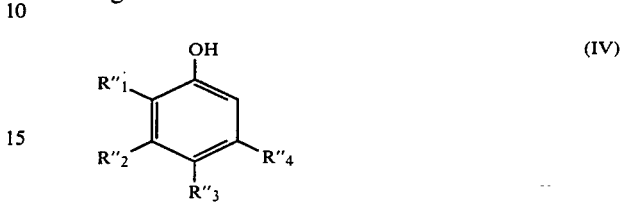
(IV)

wherein $R''_1$, $R''_2$, $R''_3$ and $R''_4$ have the same meanings as above, with an amino acid or peptide of the general formula:

HO—A—B (V), wherein A and B have the same meanings as above, or with an appropriate reactive derivative thereof, employing methods which are conventional in peptide chemistry.

The reactive derivatives used can be, for example, acid chlorides or mixed anhydrides conventionally used in peptide syntheses, such as those with ethyl chloroformate, or active esters.

Therefore, the present invention also provides the new esters of general formula (III) and is also concerned with the use thereof for the production of agents for the detection of esterolytic and/or proteolytic enzymes.

By halogen in the definition of $R_1$, $R_2$, $R_3$, $R_4$ and $R_5$ and of $R'_1$, $R'_2$, $R'_3$ and $R'_4$ there is to be understood fluorine, chlorine, bromine and iodine, chlorine and bromine being preferred.

The lower alkyl, alkoxy, alkylthio, alkylamino and dialkylamino radicals in the definitions of $R_1$–$R_5$, $R'_1$–$R'_4$ and $R''_1$–$R''_4$ contain up to 5 and preferably up to 3 carbon atoms, the methyl radical being particularly preferred.

The stabilizing anion X is preferably the tetrafluoroborate, tetrachlorozincate or perchlorate anion.

By aralkoxy radicals in the definition of $R'_1$, $R'_2$, $R'_3$ and $R'_4$, as well as aralkyl radicals in the definition of X', there are to be understood, for example, phenyl or naphthyl radicals substituted by oxy-lower-alkyl or lower alkyl radicals, the alkyl moiety thereby containing up to 5 and preferably up to 3 carbon atoms, the benzyloxy and benzyl radicals being especially preferred.

The lower acylamino radicals in the definition of $R'_1$, $R'_2$, $R'_3$ and $R'_4$ may be amido groupings of lower aliphatic carboxylic acids containing up to 5 and preferably up to 3 carbon atoms, the acetylamino radical being preferred.

The acyl radicals in the definition of X' may be the residues of aliphatic carboxylic acids containing up to 5 and preferably up to 3 carbon atoms or also of aromatic carboxylic acids, for example of benzoic or naphthoic acids, the acetyl and benzoyl radicals being especially preferred.

The aryl and aralkyl radicals in the definition of $R'_1$, $R'_2$, $R'_3$, $R'_4$ and $X'$ are preferably phenyl, naphthyl and benzyl radicals.

The amino acid residues in the definition of A, are preferably residues of naturally-occurring α-amino acids in their L- or D-form or also in their racemic form. The residues of glycine, alanine, valine, leucine, isoleucine, phenylalanine and tyrosine are especially preferred, the L-forms thereof being more especially preferred. Any free hydroxyl groups possibly present may be acylated and preferably acetylated.

The peptide residues in the definition of A are to be understood to be, for example, di-, tri-, tetra- and pentapeptides, di- and tripeptides being preferred, the amino acid components thereof preferably being the above-mentioned amino acids.

The nitrogen protective groups conventional in peptide chemistry in the definition of B are to be understood to be, for example, acyl, oxycarbonyl, thiocarbonyl, sulphonyl, sulphenyl, vinyl, cyclohexenyl, phosphoryl and carbamoyl radicals.

The diazonium salts of general formula (I) and the esters of general formulae (II) and (III) used according to the present invention may be used in concentrations of from $10^{-4}$ mol/l. to $10^{-1}$ mol/l., and preferably of from $10^{-3}$ mol/l. to $10^{-2}$ mol/l. of impregnation solution, coating mass or fluid to be investigated.

A further component of the agent according to the present invention for the detection of proteolytic enzymes and especially of the leukocyte proteases is an appropriate buffer system. For this purpose, use may be made, for example, of phosphate, borate, barbiturate, tris-(hydroxymethyl)aminomethane (tris), 2-amino-2-methylpropane-1,3-diol (amediol) or amino acid buffers, the pH value and the capacity being so chosen that a pH value of from 6 to 10 and preferably of 7 to 9 is obtained in the measurement solution or on the test strips.

A further component of the agent according to the present invention for the detection of proteolytic enzymes may be a wetting agent since a more homogeneous color distribution and, in some cases, more brilliant colors can thereby be achieved. Use can be made of cationic but also of anionic as well as amphoteric wetting agents in concentrations of from 0.05 to 2% w/v and preferably of 0.1 to 1% w/v.

A further component of the agents according to the present invention may be a phosphoric or phosphonic acid amide as a stabilizer of the general formula:

(VI)

wherein $R_6$ is a dialkylamino, alkoxy, aryloxy, alkyl, aryl, or N-morpholino radical and $R_7$ and $R_8$, which can be the same or different, are dialkylamino or N-morpholino radicals.

The alkoxy and alkyl radicals in the definition of $R_6$ are hydrocarbon radicals containing up to 10 carbon atoms.

The aryl and aryloxy radicals in the definition of $R_6$ are to be understood to be phenyl or naphthyl radicals, optionally substituted by halogen, lower alkyl or alkoxy radicals.

With the help of the compounds of general formula (VI), an astonishingly good stabilization of the formulations can be achieved.

The phosphoric and phosphonic acid amides of general formula (VI) are known compounds and are used, for example, in Federal Republic of Germany Patent Specification No. 22 35 127 as stabilizers for test strip formulations which function on the basis of a peroxidase detection.

The stabilizers of the phosphoric and phosphonic acid amide type of general formula (VI) may be added to the aqueous or preferably organic impregnation solution in concentrations of from 1 to 20% w/v and preferably of from 5 to 15% w/v.

Surprisingly, we have found that the reaction times of the diagnostic agent according to the present invention for the detection of proteolytic enzymes and especially of proteolytic leukocyte enzymes can be considerably shortened when, in addition to the diazonium salts, esters and above-mentioned adjuvants, one or more activators are also added. Activators which may be used for the agent according to the present invention are the compounds described and claimed in Federal Republic of Germany Patent Specification No. 29 05 531.

The activators are introduced into the impregnation solution in concentrations of from 0.5 to 10% w/v and preferably of from 1 to 5% w/v.

For the production of the agent according to the present invention, an absorbent carrier, preferably filter paper, cellulose or synthetic resin fiber fleece, is, for example, impregnated with solutions of the necessary reagents conventionally used for the production of test strips (substrate, buffer, optionally wetting agent) in readily volatile solvents, for example water, methanol, ethanol or acetone. This is preferably carried out in two separate steps: impregnation is first carried out with an aqueous solution which contains the buffer and other water-soluble additive materials. Thereafter, it is impregnated with a solution of the protease substrate of general formula (II) or (III), diazonium salts of general formula (I) and activators. However, the impregnation can also take place in a different sequence or with a different composition of the two impregnation solutions.

The finished test papers can be used as such or can be stuck in known manner on to handles or preferably can be sealed between synthetic resins and fine-mesh materials according to Federal Republic of Germany Patent Specification No. 21 18 455.

For the production of film-coated test strips, all the reagents are introduced into a solution or dispersion of a film-forming substance, for example a polyvinyl ester or a polyamide, and homogeneously mixed. The mixture is then coated in a thin layer on to a synthetic resin carrier and dried. After drying, the film-coated test strips according to the present invention are cut up and used as such or are stuck in known manner on to handles or sealed, for example, between synthetic resin films and fine-mesh materials according to Federal Republic of Germany Patent Specification No. 21 18 455.

The diagnostic agent according to the present invention for the detection of proteolytic enzymes and especially of leukocyte proteases can be produced in the form of powder mixtures or reagent tablets by mixing the above-mentioned components of the test with conventional galenical additives and then granulated. Additional materials of this kind include, for example, carbohydrates, such as mono-, oligo- and polysaccharides, and sugar alcohols, such as mannitol, sorbitol and xylitol, or other soluble and inert compounds, such as polyethylene glycols and polyvinylpyrrolidone. In general, the powder mixtures or reagent tablets have an end weight of about 50 to 200 mg. and preferably of 50 to 80 mg.

For the production of lyophilizates with a total weight of, in each case, about 5 to 20 mg. and preferably of about 10 mg., a solution is freeze dried which, besides all the reagents required for the test, contains conventional structure formers, for example polyvinylpyrrolidone, and optionally further filling materials, for example mannitol, sorbitol or xylitol.

The diagnostic agent according to the present invention in the form of a solution preferably contains all the reagents required for the test. The solvent used can be water or a mixture of water with a water-soluble organic solvent, for example, methanol, ethanol, acetone or dimethylformamide. For reasons of storage stability, it can be advantageous to divide up the reagents required for the test into two or more solutions which are first brought together when carrying out the actual investigation.

The diagnostic agents thus produced permit, after dipping into or after adding to the body fluid in question, the detection of the presence of proteolytic enzymes and especially of leukocyte proteases, quickly and simply by means of a color formation which can be assessed visually or photometrically, for example remission photometrically or in a cuvette. Since the activity of the leukocyte proteases per cell can be regarded as being a substantially constant value, from the intensity of the color formation there can be determined the leukocyte concentration of the body fluid being investigated. In this manner, with the diagnostic agent according to the present invention, there can be determined not only intact but also lysed leukocytes, since the activity of the leukocyte proteases is maintained even after lysis of the leukocytes. Consequently, a lysis error does not occur.

The following examples are given for the purpose of illustrating the present invention:

EXAMPLE 1

Filter paper (for example Schleicher & Schüll 23 SL) is successively impregnated with the following solutions and then dried at 60° C.:

Solution 1

0.2 molar borax-hydrochloric acid buffer pH 8
10% phosphoric acid trimorpholide

Solution 2

$2 \times 10^{-3}$ mol/l. of substrate
$10^{-2}$ mol/l. of diazonium salt dissolved in acetone decan-1-ol, 98:2 v/v Substrates S 1: 3-[N-(toluene-4'-sulphonyl)-L-alanyloxy]-indole
S 2: 3-[N-(toluene-4'-sulphonyl)-L-alanyloxy]-1-methoxynaphthalene
S 3: 1-[N-(toluene-4'-sulphonyl)-L-alanyloxy]-4-methoxynaphthalene
S 4: 1-[N-(toluene-4'-sulphonyl)-L-alanyloxy]-4-isopropoxynaphthalene
S 5: 1-[N-(toluene-4'-sulphonyl)-L-alanyloxy]-4-pentoxynaphthalene
S 6: 1-[N-(toluene-4'-sulphonyl)-L-alanyloxy]-3-dimethylaminobenzene
S 7: 1-[N-(toluene-4'-sulphonyl)-L-alanyloxy]-3-diethylaminobenzene
S 8: 1-[N-(toluene-4'-sulphonyl)-L-alanyloxy]-3,5-dimethoxybenzene
S 9: 1-[N-(toluene-4'-sulphonyl)-L-alanyloxy]-3-methyl-5-methoxybenzene Diazonium salts D 1: 2,4-dimethoxybenzenediazonium tetrafluoroborate
D 2: 4-methoxynaphthalene-1-diazonium tetrafluoroborate
D 3: 2,5-dimethoxy-4-dimethylaminobenzenediazonium tetrafluoroborate
D 4: 4-dimethylaminobenzenediazonium tetrafluoroborate Papers are obtained which, upon dipping into leukocyte containing urines, indicate 100 leukocytes/μl. in about 3 minutes with the colors indicated in the following table. The assessment can also be carried out by remission photometry.

TABLE

| substrate | diazonium salt | colour |
|---|---|---|
| S 1 | D 1 | red-brown |
| S 1 | D 2 | red-brown |
| S 1 | D 3 | blue-grey |
| S 1 | D 4 | green |
| S 2 | D 1 | red |
| S 2 | D 2 | bright red |
| S 2 | D 3 | violet |
| S 2 | D 4 | lilac |
| S 3 | D 1 | red-violet |
| S 3 | D 2 | violet |
| S 3 | D 3 | blue-grey |
| S 4 | D 1 | lilac |
| S 5 | D 1 | lilac |
| S 6 | D 1 | bright red |
| S 7 | D 1 | bright red |
| S 8 | D 1 | red-violet |
| S 9 | D 1 | red-brown |

EXAMPLE 2

Filter paper is successively impregnated with the following solutions and then dried at 60° C.:

Solution 1

0.1 molar borate buffer, pH 8

Solution 2

$2 \times 10^{-3}$ mol/l. 2-methoxy-4-(N-morpholino)-benzenediazonium tetrachlorozincate
$2 \times 10^{-3}$ mol/l. substrate+
10% phosphoric acid trimorpholide in ethanol/decan-1-ol, 98:2 v/v +Substrate A: 3-[N-benzyloxycarbonyl-L-alanyloxy]-indole
B: 3-[N-benzyloxycarbonyl-L-alanyloxy]-methylindole
C: 3-[N-benzyloxycarbonyl-L-alanyloxy]-7-methylindole
D: 3-[N-benzyloxycarbonyl-L-alanyloxy]-4-chloroindole
E: 3-[N-benzyloxycarbonyl-L-alanyloxy]-5-bromoindole
F: 3-[N-(toluene-4'-sulphonyl)-L-alanyloxy]-indole
G: 3-[N-(toluene-4'-sulphonyl)-L-alanyloxy]-5-methoxyindole H: 3-[N-(4'-acetamidobenzenesulphonyl)-L-alanyloxy]-indole
I: 3-[N-(4'-methoxytosyl)-L-alanyloxy]-indole
K: [N-(toluene-4'-sulphonyl)-L-alanyloxy]-benzene
L: 1-[N-(toluene-4'-sulphonyl)-L-alanyloxy]-naphthalene
M: 1-[N-(toluene-4'-sulphonyl)-L-alanyloxy]-3-methoxybenzene.

With the reagent papers thus obtained, 100 leukocytes/μl. can be detected in leukocyte-containing urines.

Reagent papers with comparable activity can also be obtained when, instead of the above-mentioned diazonium salts, the following are used:

2-methoxy-4-(N-pyrrolidino)-benzenediazonium tetrafluoroborate
2-methoxy-4-(N-piperidino)-benzenediazonium tetrafluoroborate
2,6-dimethoxy-4-(N-morpholino)-benzenediazonium tetrafluoroborate
4-methoxy-2-(N-morpholino)-benzenediazonium tetrafluoroborate
2-methoxy-4-[N-(N'-methyl)-piperazino]-benzenediazonium tetrafluoroborate
2-methoxy-4-(N-thiomorpholino)-benzenediazonium tetrafluoroborate.

EXAMPLE 3

The following stock solutions are prepared:

Solution 1

$2 \times 10^{-3}$ mol/l. 1-[N-(toluene-4'-sulphonyl)-L-alanyloxy]-4-isopropoxynaphthalene
$10^{-2}$ mol/l. 2,4-dimethoxybenzenediazonium tetrafluoroborate
in acetone/decan-1-ol, 98:2 v/v Solution 2

0.2 molar borax-hydrochloric acid buffer
10% phosphoric acid trimorpholide

After the activators listed below have been added either to Solution 1 or to Solution 2 in the stated concentrations, filter papers were impregnated with Solutions 1 and 2 and, in each case, dried at 60° C.

When testing in isotonic sodium chloride solution containing 300 leukocytes/μl., the tests reacted in the stated times:

| activator | mg. activator added to 20 ml. of | | reaction time in sec. |
|---|---|---|---|
| | Solution 1 | Solution 2 | |
| without | — | — | 54 |
| 4-azafluorene | 33 | — | 17 |
| benzo-(h)-quinoline | 36 | — | 8 |
| quinine | 33 | — | 32 |
| 1,2-bis-4-pyridyl-ethylene | 37 | — | 34 |
| decan-1-ol | 400 | — | 5 |
| tetradecan-1-ol | 400 | — | 4 |
| sodium nitroferricyanide | — | 31 | 38 |
| potassium hexacyanoferrate (II) | — | 40 | 30 |

EXAMPLE 4

Filter paper was impregnated with the following solutions and, after each impregnation, dried at 60° C.:

Solution 1

$2 \times 10^{-3}$ mol/l. 3-(N-toluene-4'-sulphonyl-L-alanyloxy)-indole
$2 \times 10^{-3}$ mol/l. 2-methoxy-4-(N-morpholino)-benzenediazonium tetrachlorozincate
in acetone/decan-1-ol, 98:2 v/v Solution 2

0.2 molar borax-hydrochloric acid buffer, pH 8
10% phosphoric acid trimorpholide In a further experiment, the phosphoric acid trimorpholide was omitted from Solution 2.

The test papers with phosphoric acid trimorpholide remained, after storage at 60° C. for 2 days, uncolored and gave good reactions with leukocyte-containing solutions. The test papers without phosphoric acid trimorpholide showed grey discolorations.

EXAMPLE 5

A reagent tablet was produced in a known manner containing the following components:

2 mg. 3-(N-toluene-4'-sulphonyl-L-alanyloxy)-indole
2 mg. 2-methoxy-4-(N-morpholino)-benzenediazonium tetrachlorozincate
1.5 mg. potassium dihydrogen phosphate
30 mg. disodium hydrogen phosphate dihydrate
20 mg. mannitol.

These tablets were dissolved in leukocyte-containing urine and well mixed up. When leukocytes were present, a red-violet coloration was obtained. In this manner, 100 leukocytes can be detected in about 2 minutes.

If, before the addition of the tablet, the urine was warmed to 37° C. and kept at this temperature during the reaction, then, in the same period of time, 20 leukocytes could be detected.

EXAMPLE 6

1-[N-(Toluene-4'-sulphonyl)-L-alanyloxy]-3,5-dimethoxybenzene

For reaction by the active ester process, 14.6 g. (0.06 mol) N-(toluene-4-sulphonyl)-L-alanine and 12.2 g. (0.09 mol) N-hydroxybenzotriazole are dissolved in 300 ml. anhydrous ethyl acetate, cooled to 0° C. and mixed with 12.4 g. (0.06 mol) dicyclohexylcarbodiimide. For the formation of the active ester, the reaction mixture is stirred for 2 hours at 0° C. and then for a further 2 hours at ambient temperature. After the addition of 6.2 g. (0.04 mol) 3,5-dimethoxyphenol and 5.5 ml. (0.04 mol) triethylamine, the reaction mixture is stirred for 15 hours at ambient temperature. The N,N'-dicyclohexylurea formed is filtered off with suction and the filtrate is evaporated in a vacuum at a maximum bath temperature of 50° C. The residue is taken up in 200 ml. ethyl acetate and successively washed, in each case three times, with 100 ml. amounts of 5% citric acid and then with 100 ml. amounts of 5% sodium bicarbonate solution. After drying with anhydrous sodium sulphate, the organic phase is evaporated in a vacuum. The oily crude product obtained is purified column chromatographically with a silica gel column, using toluene-ethyl acetate (4:1 v/v) as elution agent. After evaporating the appropriately collected fractions, the residue is dissolved in a little methylene chloride and the product precipitated out by the addition of diethyl ether, there being obtained 5.8 g. (38% of theory) 1-[N-(toluene-4'-sulphonyl)-L-alanyloxy]-3,5-dimethoxybenzene in the form of colorless crystals; m.p. 110° C.; $\alpha_D^{20}$: −52.5° (c=1% in acetone).

The following compounds are obtained in an analogous manner by reacting N-(toluene-4-sulphonyl)-L-alanine with the appropriately substituted phenols or naphthols:

6.1. [N-(toluene-4'-sulphonyl)-L-alanyloxy]-benzene
colorless crystals; m.p. 113° C.
$\alpha_D^{20}$: −63.8° (c=1% in acetone)

6.2. 1-[N-(toluene-4'-sulphonyl)-L-alanyloxy]-3-dimethylaminobenzene
colorless, amorphous powder
$\alpha_D^{20}$: −36.6° (c=1% in methanol)
TLC: finished plate silica gel (elution agent: toluene-dioxan 2:1 v/v; detection: UV; $R_F$ value: 0.68)

6.3 1-[N-(toluene-4'-sulphonyl)-L-alanyloxy]-3-methoxybenzene
colorless, crystals, m.p. 60°–61° C.
$\alpha_D^{20}$: −62.9° (c=1% in methanol)

6.4. 1-[N-(toluene-4'-sulphonyl)-L-alanyloxy]-naphthalene
colorless, viscous oil
$\alpha_D^{20}$: −27.3° (c=1% in methanol)
TLC: finished plate silica gel (elution agent: toluene-dioxan 4:1 v/v; detection: UV; $R_F$ value: 0.53)

6.5. 1-[N-(toluene-4'-sulphonyl)-L-alanyloxy]-4-methoxynaphthalene
colorless crystals, m.p. 136° C.
$\alpha_D^{20}$: −42.6° (c=1% in acetone)

6.6. 1-[N-(toluene-4'-sulphonyl)-L-alanyloxy]-4-isopropoxynaphthalene
colourless cyrstals, m.p. 93°–96° C.
$\alpha_D^{20}$: −38.0 (c=1% in acetone)

6.7. 1-[N-(toluene-4'-sulphonyl)-L-alanyloxy]-4-pentoxynaphthalene
colorless crystals, m.p. 87° C.
$\alpha_D^{20}$: −36.9° (c=1% in acetone)

6.8 1-[N-(toluene-4'-sulphonyl)-L-alanyloxy]-3-diethylaminobenzene
colorless: crystals, m.p. 83°–84° C.
$\alpha_D^{20}$: −59.4° (c=1% in methanol)
TLC: finished plate silica gel (elution agent xylene-methyl ethyl ketone 1:1 v/v; $R_F$ value 0.68)

6.9. 1-[N-(toluene-4'-sulphonyl)-L-alanyloxy]-3-methyl-5-methoxybenzene
colorless crystals, m.p. 79°–81° C.
$\alpha_D^{20}$: −62.2° (c=1% in methanol)
TLC: finished plate silica gel (elution agent chloroform-methanol 20:1 v/v; $R_F$ value 0.79).

EXAMPLE 7

2-[N-(Toluene-4'-sulphonyl)-L-alanyloxy]-4-methoxynaphthalene

Solution 1

For the preparation of the acid chloride by the one-step method, 19.44 g. (0.08 mol) N-(toluene-4-sulphonyl)-L-alanine are dissolved in 100 ml. anhydrous dimethylformamide and cooled to −20° C. 5.81 ml. (0.08 mol) Thionyl chloride are then pipetted thereto, with stirring and cooling, and the reaction mixture left to stand for 30 minutes in a cold bath at −20° C.

Solution 2

11.0 ml. (0.08 mol) Triethylamine are added to a solution of 6.96 g. (0.04 mol) 4-methoxynaphth-2-ol in 50 ml. anhydrous dimethylformamide. The mixture is then cooled to −20° C.

Reaction

Solution 1 is poured into Solution 2 and the mixture stirred, with the exclusion of water, for about 4 hours at −20° C., whereafter the reaction mixture is left to stand overnight in a refrigerator.

For working up, the reaction solution is evaporated in a vacuum at a maximum bath temperature of 50° C. The residue is taken up in about 150 ml. ethyl acetate and successively washed, in each case three times, with 100 ml. amounts of 5% citric acid solution and then with 100 ml. amounts of 5% sodium bicarbonate solution. After drying with anhydrous sodium sulphate, the organic phase is evaporated in a vacuum. The crude product is purified column chriomatographically with a silica gel column using a toluene-ethyl acetate mixture (4:1 v/v). After evaporating the appropriately collected fractions in a vacuum, the residue is dissolved in a little methylene chloride and then the product is precipitated out with a diethyl ether-ligroin mixture (1:2 v/v), there being obtained 2.8 g. (18% of theory) 2-[N-(toluene-4'-sulphonyl)-L-alanyloxy]-4-methoxynaphthalene in the form of colorless crystals; m.p. 119° C.; $\alpha_D^{20}$: −57.9° (c=1% in acetone).

EXAMPLE 8

2-Methoxy-4-(N-morpholino)-benzenediazonium tetrachlorozincate

5-Chloro-2-nitroanisole is reacted with a 1.5 molar excess of morpholine in toluene as solvent, by heating under reflux for several hours (10 to 14 hours). If desired, the reaction can also be carried out using morpholine as the solvent. For this purpose, 5-chloro-2-nitroanisole is mixed with 5 to 10 fold volumes of morpholine. Possibly demethylated product is separated off by shaking with an aqueous solution of sodium hydroxide or is again methylated by reacting with diazomethane.

The nitro compound obtained is reduced in the usual manner with palladium/charcoal in methanol or with stannous chloride in hydrochloric acid to give the amine and this is then diazotized. The diazonium compound is converted in known manner into the tetrachlorozincate in hydrochloric acid solution by the addition of a concentrated zinc chloride solution or into the tetrafluoroborate by the addition of tetrafluoroboric acid, and then isolated as such.

Tetrachlorozincate: m.p. 170°–172° C.
Tetrafluoroborate: m.p. 166°–168° C.

EXAMPLE 9

4-Methoxy-2-(N-morpholino)-benzenediazonium tetrafluoroborate 18.76 g. (0.1 mol) 3-Chloro-4-nitroanisole (m.p. 52° C.) are heated under reflux for 4 hours with 87.1 g. (1 mol) morpholine. Thereafter, the reaction mixture is cooled to ambient temperature and 100 ml. ice water are added to the reaction solution. The precipitated yellow reaction product is filtered off with suction, washed with ice-cooled 10% acetic acid and the material obtained is dried in a vacuum at 60° C., 19.5 g. of a mixture of N-(3-hydroxy-6-nitrophenyl)-morpholine and N-(3-methoxy-6-nitrophenyl)-morpholine being obtained. This product is dissolved in methylene chloride and an ethereal solution of diazomethane added thereto. After standing for two days at ambient temperature, excess diazomethane is destroyed by the dropwise addition of 2N acetic acid, the organic phase is shaken up several times with 2N aqueous sodium hydroxide solution and the solvent is evaporated off in a vacuum. There are obtained 19.1 g. (80.2% of theory) N-(3-methoxy-6-nitrophenyl)-morpholine; m.p. 84°–86° C. This substance is subsequently suspended in 250 ml. methanol and, after the addition of 1.9 g. palladium-charcoal (10%), is hydrogenated at 20° to 30° C. After filtering off the catalyst with suction, the filtrate is substantially evaporated and the liberated base is converted, by the addition of ethereal hydrochloric acid, into the hydrochloride. There are obtained 20.6 g. (73.1% of theory) of crystalline N-(3-methoxy-6-aminophenyl)-morpholine dihydrochloride; m.p. 237°–240° C.

This substance is suspended at $-5°$ C. in 96 ml. 6N hydrochloric acid and a solution of 6 g. sodium nitrite in 12 ml. water added dropwise thereto in the course of 30 minutes. The resulting brown-red diazonium salt solution is added at 0° C., while stirring, to 120 ml. 35% tetrafluoroboric acid. After standing for several hours, there are obtained 19.5 g. (63.5% of theory) 4-methoxy-2-(N-morpholino)-benzenediazonium tetrafluoroborate in the form of yellow crystals; m.p. 115°–116° C. (decomp.).

The following compounds are obtained in an analogous manner:

(a) 2-Methoxy-4-(N-thiomorpholino)-benzenediazonium tetrafluoroborate (m.p. 106°–108° C. (decomp.)) from 5-chloro-2-nitroanisole and thiomorpholine.

The intermediate product, 2-amino-5-(N-thiomorpholino)-anisole dihydrochloride is prepared in the following manner:

Into a 1 liter three-necked flask equipped with a stirrer, there are introduced 100 g. stannous chloride dihydrate in 400 ml. 6N hydrochloric acid and 25.4 g. (1 mole) 2-nitro-5-(N-thiomorpholino)-anisole are introduced portionwise at ambient temperature, while stirring. The reaction mixture is thereafter heated for 30 minutes at 75° C., cooled to ambient temperature and the reaction solution added dropwise to 750 ml. 30% aqueous sodium hydroxide solution, with ice cooling. The liberated base is extracted several times with diethyl ether and, after drying and partial evaporation of the solvent, is converted into the hydrochloride by adding ethereal hydrochloric acid. There are obtained 24.9 g. (83.8% of theory) 2-amino-5-(N-thiomorpholino)-anisole dihydrochloride; m.p. 218°–220° C.

(b) 2-Methoxy-4-(N-piperidino)-benzenediazonium tetrafluoroborate (m.p. 123°–125° C. (decomp.)) from 5-chloro-2-nitroanisole and piperidine);

(c) 2-Methoxy-4-(N-pyrrolidino)-benzenediazonium tetrafluoroborate (m.p. 137°–139° C. (decomp.)) from 5-chloro-2-nitroanisole and pyrrolidine;

(d) 2-Methoxy-4-[N-(N′-methyl)-piperazino]-benzenediazonium tetrafluoroborate dihydrotetrafluoroborate (m.p. 163° C. (decomp.)) from 5-chloro-2-nitroanisole and N-methylpiperazine.

In the preparation of this compound, the diazotisation is carried out with amyl nitrite in methanol. For this purpose, 39.6 g. (0.1 mol) 2-amino-5-(N-methylpiperazino)-anisole dihydrotetrafluoroborate are dissolved in 175 ml. methanol, 11.6 g. (0.1 mol) amyl nitrite in 25 ml. methanol are added thereto and 60 ml. 35% tetrafluoroboric acid slowly added dropwise thereto at 0° C., while stirring. Upon standing, 24.8 g. (51.7% of theory) 2-methoxy-4-[N-(N′-methyl)-piperazino]-benzenediazonium tetrafluoroborate dihydrotetrafluoroborate crystallize out in the form of brownish crystals; m.p. 163° C. (decomp.).

(e) 2-Methoxy-4-(N-morpholino)-benzenediazonium tetrafluoroborate (m.p. 166°–168° C. (decomp.)) from 5-chloro-2-nitroanisole and morpholine.

It will be understood that the specification and examples are illustrative but not limitative of the present invention and that other embodiments within the spirit and scope of the invention will suggest themselves to those skilled in the art.

What is claimed is:

1. Agent for the detection of esterolytic and proteolytic enzymes comprising an esterase or protease or combination thereof, detection reagent and a buffer, the detection reagent being a combination of a substituted diazonium salt and an ester compound; wherein said diazonium salt is a compound of the formula:

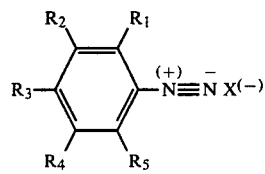

in which $R_1$ is a lower alkyl, lower alkoxy, lower alkylthio, N-morpholino, N-thiomorpholino, N-pyrrolidino, N-alkylated N-piperazino, N-piperazino or N-piperidino radical or is a halogen or hydrogen atom;

$R_3$ is a lower alkyl, lower alkoxy, aryloxy, lower alkylthio, alkylamino, dialkylamino, hydroxyl, N-morpholino, N-thiomorpholino, N-pyrrolidino, N-piperazino, N′-alkylated N-piperazino, N-piperidino or phenylamino radical or a phenyl radical or phenyl substituted with a lower alkyl or lower alkoxy radical, or is a hydrogen or halogen atom;

$R_2$, $R_4$ and $R_5$, which may be the same or different, are lower alkyl, lower alkoxy or lower alkylthio radicals or halogen or hydrogen atoms; and X is a stabilizing anion; and said ester is a compound of the formula:

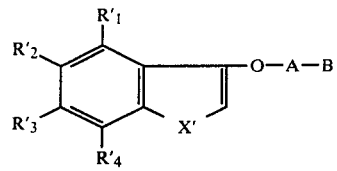

in which $R'_1$, $R'_2$, $R'_3$ and $R'_4$, which may be the same or different, are hydrogen or halogen atoms or lower alkyl, lower alkoxy, aryl, aralkyl, aralkoxy, hydroxyl, carboxy, carboxy lower alkoxy, aralkoxycarbonyl, aralkoxycarbonyl lower alkoxy, nitro, alkylamino, dialkylamino or acylamino radicals or in which two adjacent substituents represent a fused benzene ring or a halogen-substituted fused benzene ring;

X′ is a sulfur atom or an imino group optionally substituted by lower alkyl, aryl, aralkyl or acyl radical;

A is an acyl residue of an amino acid or of a peptide; and

B is a nitrogen protective group or derived therefrom or a compound of the formula

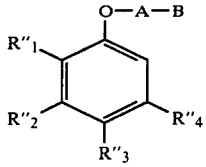

wherein

R″1, R″2, R″3 and R″4, which may be the same or different, are hydrogen atoms or lower alkyl, lower alkoxy, alkylamino or dialkylamino radicals or in which two adjacent substituents can also represent a fused benzene ring;

A is an acyl residue of an amino acid or of a peptide; and

B is a nitrogen protective group conventional in peptide chemistry or derived therefrom.

2. Agent as claimed in claim 1 wherein said detection reagent and buffer are impregnated onto an absorbent carrier.

3. Agent as claimed in claim 1 wherein said detection reagent and buffer are contained in a film layer.

4. Agent as claimed in claim 1 wherein said detection reagent and buffer are in the form of a powder mixture.

5. Agent as claimed in claim 1 wherein said detection reagent and buffer are in the form of a lyophilizate.

6. Agent as claimed in claim 1 wherein said detection reagent and buffer are in the form of a solution.

7. Agent as claimed in claim 1 wherein said detection reagent and buffer are in the form of a reagent tablet.

8. Agent as claimed in claim 1 also containing reagent adjuvants.

9. Agent as claimed in claim 1 wherein the ester is a compound of the formula

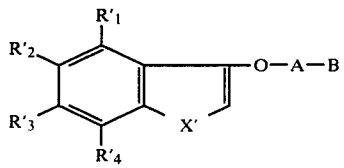

in which

R′1, R′2, R′3 and R′4, which may be the same or different, are hydrogen or halogen atoms or lower alkyl, lower alkoxy, aryl, aralkyl, aralkoxy, hydroxyl, carboxy, carboxyl lower alkoxy, aralkoxycarbonyl, aralkoxycarbonyl lower alkoxy, nitro or acylamino radicals or in which two adjacent substituents represent a fused benzene ring or a halogen-substituted fused benzene ring;

X′ is a sulfur atom or an imino grup optionally substituted by lower alkyl, aryl, aralkyl or acyl radical;

A is an acyl residue of an amino acid or of a peptide; and

B is a nitrogen protective group or derived therefrom.

10. Agent as claimed in claim 1 wherein the ester used is a compound of the formula

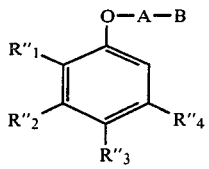

wherein

R″1, R″2, R″3 and R″4, which may be the same or different, are hydrogen atoms or lower alkyl, lower alkoxy, alkylamino or dialkylamino radicals or in which two adjacent substituents can also represent a fused benzene ring;

A is a residue of an amino acid or of a peptide; and

B is a nitrogen protective group conventional in peptide chemistry or derived therefrom.

11. Agent as claimed in claim 1 wherein, as an esterase or protease detection reagent, said agent contains a combination of a diazonium salt of the formula

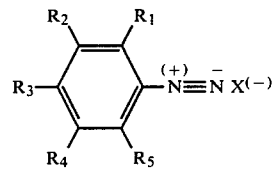

wherein $R_1$ is a lower alkyl, lower alkoxy, lower alkylthio, N-morpholino, N-thiomorpholino, N-pyrrolidino, optionally N′-alkylated N-piperazino or N-piperidino radical or is a hydrogen or halogen atom;

$R_3$ is a lower alkyl, lower alkoxy, an aryloxy, a lower alkylthio, alkylamino, dialkylamino, hydroxyl, N-morpholino, N-thiomorpholino, N-pyrrolidino, optionally N-alkylated N-piperazino, N-piperidino or phenylamino radical or a phenyl radical optionally substituted with a lower alkyl or lower alkoxy radical;

$R_2$, $R_3$ and $R_5$, which may be the same or different, are lower alkyl, lower alkoxy or lower alkylthio radicals or are hydrogen or halogen atoms; and X is a stabilizing anion;

and an ester of the formula

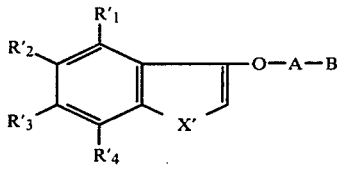

in which

R′1, R′2, R′3 and R′4, which may be the same or different, are hydrogen or halogen atoms or lower alkyl, lower alkoxy, aryl, aralkyl, aralkoxy, hydroxyl, carboxy, carboxy lower alkoxy, aralkoxycarbonyl, aralkoxycarbonyl lower alkoxy, nitro or lower acylamino radicals or in which two adjacent substituents represent an optionally halogen-substituted fused benzene ring;

X' is a sulfur atom or an imino group optionally substituted by a lower alkyl, an aryl, an aralkyl or an acyl radical;

A is an acyl residue of an amino acid or of a peptide; and

B is a nitrogen protective group conventional in peptide chemistry or derived therefrom.

12. Agent as claimed in claim 1 wherein as an esterase or protease detection reagent, said agent contains a combination of a diazonium salt of the formula

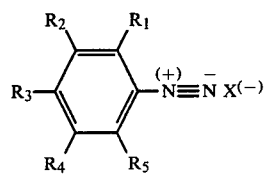

wherein $R_1$ is a lower alkyl, lower alkoxy, lower alkylthio, N-morpholino, N-thiomorpholino, N-pyrrolidino, optionally N-alkylated N-piperazino or N-piperidino radical or is a hydrogen or halogen atom;

$R_3$ is a lower alkyl, lower alkoxy, an aryloxy, a lower alkylthio, alkylamino, dialkylamino, hydroxyl, N-morpholino, N-thiomorpholino, N-pyrrolidino, optionally N-alkylated N-piperazino, N-piperidino or phenylamino radical or a phenyl radical optionally substituted with a lower alkyl or lower alkoxy radical;

$R_2$, $R_3$ and $R_5$, which may be the same or different, are lower alkyl, lower alkoxy or loer alkylthio radicals or are hydrogen or halogen atoms; and X is a stabilizing anion;
and a compound of the formula

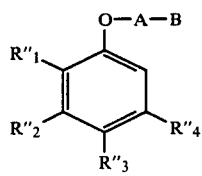

wherein $R''_1$, $R''_2$, $R''_3$ and $R''_4$, which may be the same or different, are hydrogen atoms or lower alkyl, lower alkoxy, alkylamino or dialkylamino radicals or in which two adjacent substituents represent a fused benzene ring; and A is an acyl residue of an amino acid or of a peptide; and B is a nitrogen protective group conventional in peptide chemistry or derived therefrom.

13. Agent as claimed in claim 1 wherein said ester compound is 1-[N-(toluene-4'-sulfonyl)-L-alanyloxy]-4-isopropoxynaphthalene.

14. Agent as claimed in claim 1 wherein said ester compound is selected from

3-[N-(toluene-4'-sulfonyl)-L-alanyloxy]-indole

3-[N-(toluene-4'-sulfonyl)-L-alanyloxy]-5-methoxyindole

3-[N-(4'-methoxytosyl)-L-alanyloxy]-indole and wherein the substituted diazonium salt compound is selected from 4-dimethylamino-benzene-diazonium tetrafluoroborate 2-methoxy-4-(N-morpholino)-benzenediazonium tetrachlorozincate 2-methoxy-4-(N-piperidino)-benzenediazonium tetrafluoroborate.

15. Agent as claimed in claim 14 wherein the ester compound is 3-[N-(toluene-4'-sulfonyl)-L-alanyloxy]-indole.

16. Agent as claimed in claim 14 wherein the ester compound is 3-[N-(toluene-4'-sulfonyl)-L-alanyloxy]-5-methoxyindole.

17. Agent as claimed in claim 14 wherein the ester compound is 3-[N-(4'-methoxytosyl)-L-alanyloxy]-indole.

18. Agent as claimed in claim 14 wherein said substituted diazonium salt compound is 4-dimethylaminobenzenediazonium tetrafluoroborate.

19. Agent as claimed in claim 14 wherein said substituted diazonium salt compound is 2-methoxy-4-(N-morpholino)-benzenediazonium tetrachlorozincate.

20. Agent as claimed in claim 14 wherein said substituted diazonium salt compound is 2-methoxy-4-(N-piperidino)-benzenediazonium tetrafluoroborate.

21. Method of detecting esterolytic and/or proteolytic enzymes, which method comprises contacting a sample with an agent as claimed in claim 1 and evaluating the intensity of the color formed thereby.

22. Agent as claimed in claim 1 containing at least one adjuvant selected from wetting agents, stabilizers, activators, film formers, galenical additives and structure formers.

* * * * *

UNITED STATES PATENT AND TRADEMARK OFFICE
CERTIFICATE OF CORRECTION

PATENT NO. : 4,551,428

DATED : November 5, 1985

INVENTOR(S) : Dieter Berger et al

It is certified that error appears in the above-identified patent and that said Letters Patent is hereby corrected as shown below:

```
Col. 11, line 31, "cyrstals" should be --crystals--.
Col. 11, line 40, delete ":".

Claim 12, col. 17, line 34, "loer" should be --lower--.
```

Signed and Sealed this

Fifteenth Day of April 1986

[SEAL]

Attest:

DONALD J. QUIGG

Attesting Officer

Commissioner of Patents and Trademarks